United States Patent [19]

Joullié et al.

[11] 4,252,804
[45] Feb. 24, 1981

[54] THERAPEUTICALLY USEFUL 3,4,5-TRIMETHOXYBENZENE DERIVATIVES

[75] Inventors: Maurice Joullié, Saint-Germain-en-Laye; Gabriel Maillard, Paris; Lucien Lakah, Paris; Christian J. M. Warolin, Paris, all of France

[73] Assignee: Metabio-Joullie, Meudon, France

[21] Appl. No.: 869,299

[22] Filed: Jan. 13, 1978

[30] Foreign Application Priority Data

Jan. 14, 1977 [GB] United Kingdom ............... 1605/77

[51] Int. Cl.³ ............... A61K 31/535; C07D 295/18
[52] U.S. Cl. ............... 424/248.54; 544/141; 544/137; 424/248.5; 544/124; 424/248.55; 544/111; 544/121; 424/248.56; 544/128; 544/130; 424/246; 544/131; 544/105; 424/250; 544/91; 260/326.43; 424/263; 560/29; 560/31; 424/267; 560/32; 560/27; 424/272; 564/188; 564/164; 424/274; 564/165; 564/34; 424/285; 564/143; 260/239 B; 424/283; 546/237; 546/233; 544/382; 546/221; 546/308; 544/394; 548/240; 546/159; 544/393; 546/143; 260/347.3; 544/399; 260/345.7 R; 564/189; 544/389; 564/191; 564/194; 544/58.4; 564/52; 564/79; 544/165; 564/142; 564/167; 544/172; 544/58.1; 544/85; 544/86; 544/158; 544/159; 544/168; 544/92; 544/169; 544/171; 544/87; 544/176; 544/175; 544/152; 544/149
[58] Field of Search ............... 544/58, 165, 172, 85, 544/86, 158, 159, 168, 176, 169, 175, 171; 424/248.5, 248.54, 248.55, 248.56, 246

[56] References Cited

U.S. PATENT DOCUMENTS

| | | | |
|---|---|---|---|
| 2,870,145 | 1/1959 | Perron ................... | 544/169 |
| 2,870,146 | 1/1959 | Perron ................... | 544/58 |
| 2,882,273 | 4/1959 | Holdrege ................ | 544/169 |
| 3,234,276 | 2/1966 | Petracek ................ | 544/168 |
| 3,562,262 | 2/1971 | Schmidt et al. ......... | 544/172 |
| 3,729,470 | 4/1973 | Vaille ..................... | 544/58 |
| 3,755,317 | 8/1973 | Pifferi ................... | 544/58 |

FOREIGN PATENT DOCUMENTS 872350 7/1961 United Kingdom ............ 544/172
912788 12/1962 United Kingdom .
1346029 2/1974 United Kingdom .

OTHER PUBLICATIONS

Chemical Abstracts, vol. 71, Item 29134(y) (1969), abstracting Green et al., in "J. Pharm. Pharmacol." (1969), vol. 21, No. 6, pp. 366-373.

Primary Examiner—Henry R. Jiles
Assistant Examiner—Robert T. Bond
Attorney, Agent, or Firm—Gordon W. Hueschen

[57] ABSTRACT

Compounds of the formula I

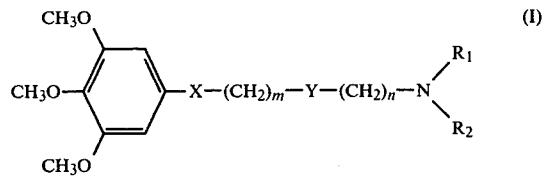

wherein m and n are 0, 1 or 2, X represents oxygen, imino, benzylimino, or morpholinoethylimino, Y represents CO, CONH, COO or SO$_2$, and NR$_1$R$_2$ represents a dimethylamino, diethylamino, dipropylamino, dibutylamino, allylamino, isobutenylamino, cyclopentylamino, cyclohexylamino, cycloheptylamino, cyclooctylamino, N-methyl N-cyclopentylamino, N-methyl N-cyclohexylamino, N-allyl N-cyclohexylamino, adamantylamino, diethoxyethylamino, dimethylaminoethylamino, dimethylaminopropylamino, N-methyl N-dimethylaminopropyl-amino, benzylamino, 3,4,5-trimethoxybenzylamino, phenethylamino, p-chlorophenethylamino, tetrahydrofurfurylamino, tetrahydropyranylmethylamino, pyrrolidino, isoxazolidinyl, piperidino, 4-hydroxypiperidino, 4-m-chlorophenyl-4-hydroxypiperidino, homopiperidino, 1,2,3,6-tetrahydropyridyl, morpholino, 2-methylmorpholino, 2,6-dimethylmorpholino, 2-morpholinoethylamino, thiamorpholino, piperazino, 4-methylpiperazino, 4-(α-m-chlorophenyl-benzyl)-piperazino, 4-(3,4,5-trimethoxyphenylaminocarbonyl)-piperazino, 4-(3,4,5-trimethoxyphenylaminocarbonylmethyl)-piperazino, 4-phenylpiperazino, 4-m-trifluoromethylphenyl-piperazino, 4-piperidinocarbonylmethyl-piperazino, 1,2,3,4-tetrahydroquinolyl, 1,2,3,4-tetrahydroisoquinolyl, (7-chloro-4-quinolyl)-amino, 1,2,3,4-tetrahydrobenzoxazinyl or 1,2,3,4-tetrahydro-6-chlorobenzoxazinyl group, and their pharmaceutically acceptable acid addition salts are novel and are therapeutically useful, in particular as tranquillizers, myorelaxants and anticonvulsants.

11 Claims, No Drawings

THERAPEUTICALLY USEFUL 3,4,5-TRIMETHOXYBENZENE DERIVATIVES

The present invention relates to derivatives of 3,4,5-trimethoxybenzene, their preparation as well as their therapeutical use, in particular as tranquillisers, myorelaxants and anticonvulsants.

According to the present invention there are provided compounds of the formula I

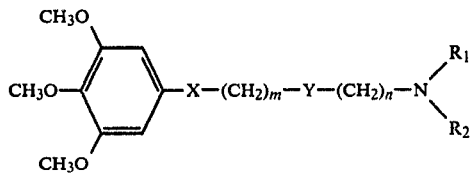

wherein
each of m and n, which may be the same or different, represents 0, 1 or 2,
X represents an oxygen atom or an imino group of formula $NR_3$ (wherein $R_3$ represents a hydrogen atom or a benzyl or morpholinoethyl group),
Y represents one of the divalent groups CO, CONH, COO or $SO_2$, and
$NR_1R_2$ represents a dimethylamino, diethylamino, dipropylamino, dibutylamino, allylamino, isobutenylamino, cyclopentylamino, cyclohexylamino, cycloheptylamino, cyclooctylamino, N-methyl N-cyclopentylamino, N-methyl N-cyclohexylamino, N-allyl N-cyclohexylamino, adamantylamino, diethoxyethylamino, dimethylaminoethylamino, dimethylaminopropylamino, N-methyl N-dimethylaminopropylamino, benzylamino, 3,4,5-trimethoxybenzylamino, phenethylamino, p-chlorophenethylamino, tetrahydrofurfurylamino, tetrahydropyranylmethylamino, pyrrolidino, isoxazolidinyl, piperidino, 4-hydroxypiperidino, 4-p-chlorophenyl-4-hydroxypiperidino, homopiperidino, 1,2,3,6-tetrahydropyridyl, morpholino, 2-methylmorpholino, 2,6-dimethylmorpholino, 2-morpholinoethylamino, thiamorpholino, piperazino, 4-methylpiperazino, 4-(α-m-chlorophenyl-benzyl)-piperazino, 4-(3,4,5-trimethoxyphenylaminocarbonyl)-piperazino, 4-(3,4,5-trimethoxyphenylaminocarbonylmethyl)-piperazino, 4-phenylpiperazino, 4-m-trifluoromethylphenyl piperazino, 4-piperidinocarbonylmethyl-piperazino, 1,2,3,4-tetrahydroquinolyl, 1,2,3,4-tetrahydroisoquinolyl, (7-chloro-4-quinolyl)-amino, 1,2,3,4-tetrahydrobenzoxazinyl or 1,2,3,4-tetrahydro-6-chlorobenzoxazinyl group,
as well as their pharmaceutically acceptable acid addition salts.

Preferred compounds of the invention are those of the formula

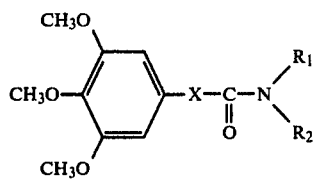

(wherein X and $NR_1R_2$ are as defined above) and their pharmaceutically acceptable acid addition salts; those of the formula

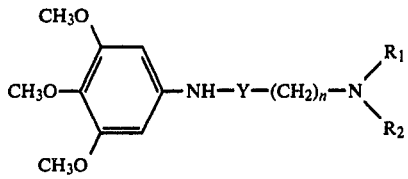

(wherein X, m and $NR_1R_2$ are as defined above) and their pharmaceutically acceptable acid addition salts; and those of the formula

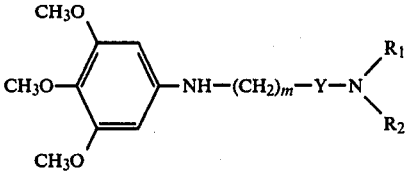

(wherein Y, n and $NR_1R_2$ are as defined above) and their pharmaceutically acceptable acid addition salts.

Preferably $NR_1R_2$ represents a dimethylamino, morpholino, 2,6-dimethylmorpholino, piperidino or 4-methylpiperazino group, especially a morpholino group.

The compounds of the formula I according to the present invention may be obtained from known compounds according to the following general scheme:

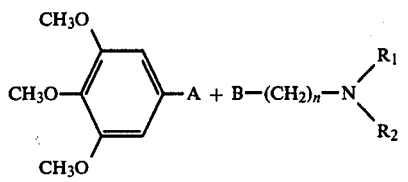

In these formulae A represents a $-N=C=O$, $NH_2$, OH or $-NH-(CH_2)_m-CO-$hal group, B represents H, $NH_2$, OH, hal$-CO-$ or hal$-SO_2-$, hal being a halogen, preferably chlorine, atom, and
$NR_1R_2$, m and n have the same meanings as in formula I.

Compounds of the formula I wherein X represents a group of formula $NR_3$ wherein $R_3$ is other than hydrogen may be prepared from the corresponding compound where $R_3$ is hydrogen.

Pharmaceutically acceptable acid addition salts may be prepared in conventional manner by reaction of a base of the formula I with a pharmaceutically acceptable acid.

The various usable reactants are illustrated in the general preparations given below. The symbols $NR_1 R_2$ and hal the same meanings as above.

(A) UREAS

When m=n=0; X=NH; Y=CO, the corresponding ureas may be prepared either by reaction of an isocyanate with an amine according to the scheme:

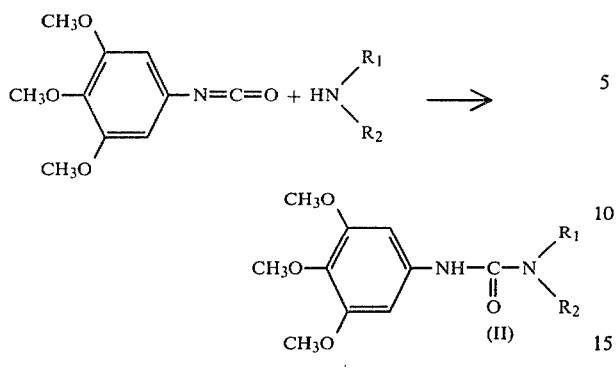

or by reaction of an aniline with an N-chloroformylated amine according to the scheme:

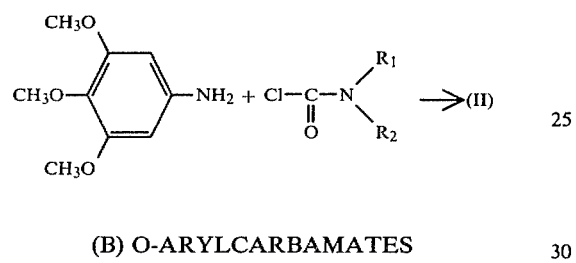

(B) O-ARYLCARBAMATES

When $m=n=0$; $X=O$; $Y=CO$, the corresponding carbamates may be prepared by reaction of a phenol (which may be in the form of a salt e.g. sodium salt) with an N-chloroformylated amine according to the scheme:

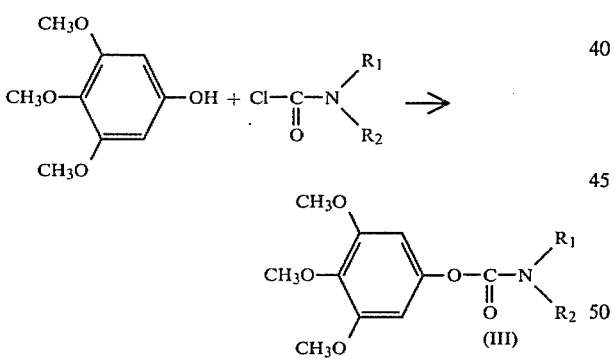

(C) SEMI CARBAZIDES

When $m=n=0$; $X=NH$; $Y=CO-NH$, the corresponding semi-carbazides may be prepared by reaction of an isocyanate with a hydrazine according to the scheme:

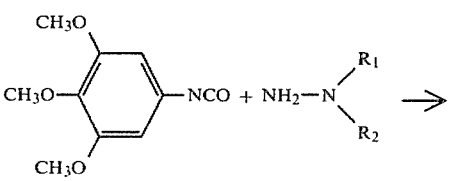

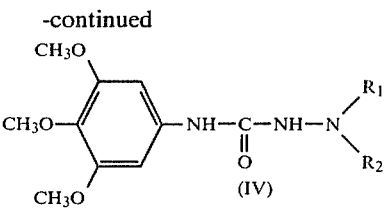

(D) N-ARYL CARBAMATES

When $m=n=0$; $X=NH$; $Y=COO$, the corresponding carbamates may be prepared by reaction of an isocyanate with a hydroxylamine according to the scheme:

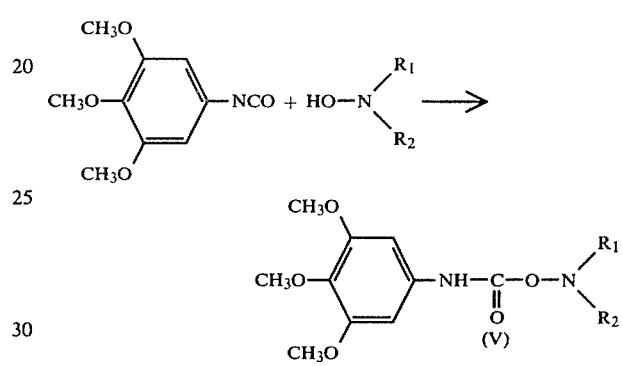

When $m=0$; $n=1$ or 2; $X=NH$; $Y=COO$, the corresponding carbamates may be prepared by reaction of an isocyanate with an alcohol according to the scheme:

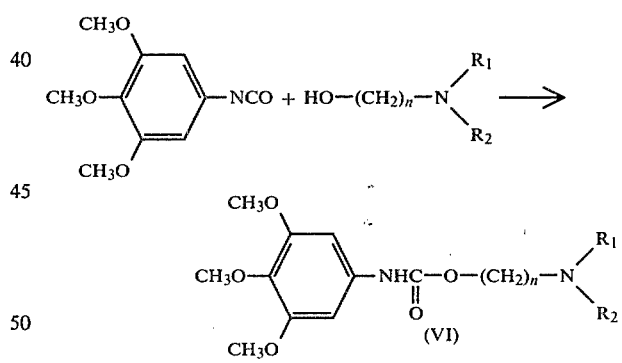

(E) SULPHAMIDES

When $m=n=0$; $X=NH$; $Y=SO_2$, the corresponding sulphamides may be prepared by reaction of an aniline with an N-chlorosulphonated amine according to the scheme:

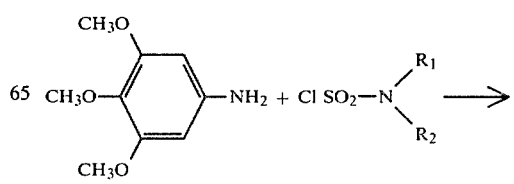

-continued

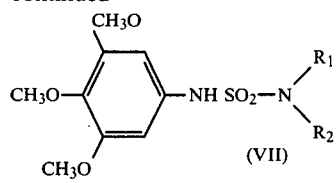

(VII)

(F) 2-ANILINO-ACETAMIDES AND 3-ANILINO-PROPIONAMIDES

When m=1 or 2; n=0; X=NH; Y=CO, the corresponding amides may be prepared by reaction of an acid halide with an amine according to the scheme:

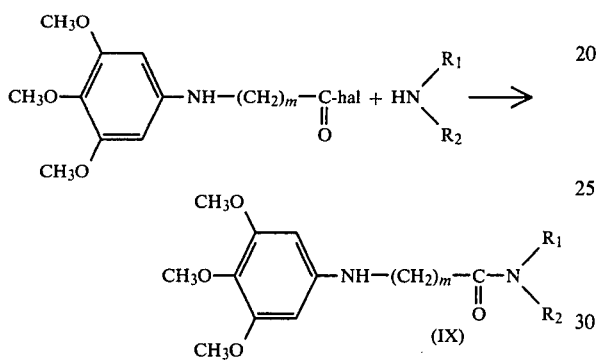

(IX)

(G) N-ARYL-ACETAMIDES AND PROPIONAMIDES

When m=0; n=1 or 2; X=NH; Y=CO, the corresponding amides may be prepared by reaction of an aniline with an acid halide according to the scheme:

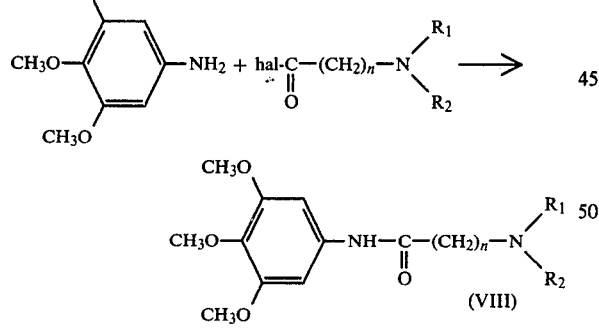

(VIII)

The invention also provides a pharmaceutical composition which contains a compound of the formula I or a pharmaceutically acceptable acid addition salt thereof, together with a pharmaceutically acceptable carrier or diluent.

The invention further provides a method of treating a human patient which method comprises administering to the patient a compound of the formula I or a pharmaceutically acceptable acid addition salt thereof.

The following non-limiting Examples illustrate the invention.

EXAMPLE 1

2,6-Dimethyl-4-[N-(3,4,5-trimethoxyphenyl)-carbamoyl]-morpholine. ($C_{16}H_{24}N_2O_5 = 324.38$)

To a stirred solution of 4.0 g (0.019 mole) 3,4,5-trimethoxyphenyl-isocyanate in 100 ml anhydrous ether are added 2.4 g (0.021 mole) 2,6-dimethylmorpholine. The mixture is heated at the reflux temperature of the solvent, with stirring, for 7 hours.

After cooling, the precipitate is dried, washed with ether and dried. The colourless liquid thus obtained (4.9 g; 79% yield) is recrystallised from water to give the pure product which melts at 117°–118° C.

EXAMPLE 2

1-Methyl-4-[N-(3,4,5-trimethoxyphenyl)-carbamoyl]-piperazine (hydrochloride)

A solution of 10 g (0.061 mole) 1-methyl-4-chloroformyl-piperazine in 100 ml dry methylene chloride is added to a solution of 11.2 g (0.061 mole) 3,4,5-trimethoxy-aniline in a 100 ml methylenechloride. After stirring at ambient temperature for 24 hours, the solvent is evaporated off in vacuo; the residue is dissolved in the minimum of ethanol and then the crude hydrochloride precipitated by the addition of diethyl ether, and dried.

Purification by recrystallisation from an acetone 3-ethanol 1 mixture gives the pure product (9.4 g; 44% yield) which melts at 184°–86° C.

EXAMPLE 3

4-(3,4,5-Trimethoxyphenoxycarbonyl)-morpholine ($C_{14}H_{19}NO_6 = 297.31$)

To a solution of 10.15 g (0.049 mole) sodium 3,4,5-trimethoxyphenolate in 100 ml anhydrous dimethylformamide are added gradually, with stirring, 7.5 g (0.050 mole) N-chloroformyl-morpholine.

The reaction is clearly exothermic. After the completion of the addition, the mixture is heated at about 50° C. for 2 hours. The sodium chloride is then separated off by filtration and the solvent evaporated off in vacuo.

The solid obtained by washing of the crude product with water is recrystallised from ethanol to give 9.6 g pure product (65% yield) melting at 118°–119° C.

EXAMPLE 4

N-(3,4,5-trimethoxyphenyl) N'-morpholino-urea. ($C_{14}H_{21}N_3O_5 = 311.34$)

A solution of 2.6 g (0.025 mole) 4-aminomorpholine in 50 ml anhydrous ether is added, with stirring, to a solution of 5.0 g (0.024 mole) 3,4,5-trimethoxyphenyl-isocyanate in 200 ml dry ether.

The solution is then heated at the reflux of the solvent, with stirring, for 4 hours 30 minutes. After cooling, the precipitate is dried and washed with ether. The colourless solid obtained (7.0 g: 94% yield) is purified by recrystallisation from water. Melting point=204° C.

EXAMPLE 5

N-(2-morpholino-ethoxycarbonyl)-3,4,5-trimethoxyaniline. ($C_{16}H_{24}N_2O_6 = 340.38$)

A solution of 5.0 g (0.024 mole) 3,4,5-trimethoxyphenyl-isocyanate and 3.4 g (0.026 mole) 4-(2-hydroxyethyl)-morpholine in 300 ml anhydrous ether is heated under reflux, with stirring, for 7 hours.

The solvent is evaporated off under vacuum and then the oily residue is triturated in isopropyl ether.

The crystals obtained are dried to give 5.5 g (67% yield) of a colourless solid. Purification is readily effected by silica chromatography (Merck 7754) using ethyl acetate as eluant.

Melting point=81°-82° C.

EXAMPLE 6

4-[N-(3,4,5-trimethoxyphenyl)-sulphamoyl]-morpholine. ($C_{13}H_{20}N_2O_6S = 332.38$)

To a solution of 4.8 g (0.026 mole) 3,4,5-trimethoxyaniline and 2.6 g (0.026 mole) triethylamine in 200 ml dry benzene are added 5.7 g (0.031 mole) N-chlorosulphonyl morpholine.

The mixture obtained is heated at the reflux of the solvent, with stirring, for 14 hours. After evaporation of the solvent under vacuum, the oily residue is taken up in a mixture of water and ethyl acetate. The two phases are decanted, the organic phase washed with a 2 N-hydrochloric acid solution, dried and concentrated to dryness; the residual solid is triturated in ether and the insoluble material dried to give 4.1 g of a slightly coloured solid (47% yield). Purification is by recrystallisation from water.

Melting point=148° C.

EXAMPLE 7

4-[2-(3,4,5-trimethoxyanilino)-acetyl]-morpholine. ($C_{15}H_{22}N_2O_5 = 310.35$)

A mixture of 12.8 g (0.07 mole) 3,4,5-trimethoxyaniline, 12.6 g (0.077 mole) N-chloroacetyl-morpholine and 7.8 g (0.077 mole) triethylamine in 300 ml anhydrous benzene is heated at the reflux of the solvent, with stirring, for 14 hours.

After cooling, the triethylamine hydrochloride is separated off by filtration and then the organic phase is concentrated under vacuum.

The residual oil obtained, triturated in diethyl ether, gives on agglomeration a solid which is dried and washed with ether several times to give, after drying, 19.3 g of a slightly coloured solid (89% yield).

Purification is by silica chromatography (Merck 7754) with elution with ethyl acetate and recrystallisation from ethanol.

Melting point=136° C.

EXAMPLE 8

2-Morpholino-N-(3,4,5-trimethoxyphenyl)-acetamide

To a solution of 1.3 g (0.15 mole) morpholine and 1.6 g (0.016 mole) triethylamine in 75 ml dry benzene are added, in fractions with stirring and slight cooling, 4.3 g (0.016 mole) 2-chloro-N-(3,4,5-trimethoxyphenyl)acetamide.

After completion of the addition, the mixture is heated at the reflux of the solvent for 20 hours. After cooling, the triethylamine hydrochloride formed is dried and washed with benzene.

The organic phase is concentrated under vacuum, the residual paste obtained is recrystallised from ethanol to give 2.6 g of a slightly coloured solid (56% yield) melting at 110°-111° C.

EXAMPLE 9

N-morpholinocarbonyl, N-(2-morpholinoethyl)-3,4,5-trimethoxyaniline hydrochloride. ($C_{20}H_{31}N_3O_6 \cdot HCl = 445.95$)

Under an inert atmosphere 0.45 g sodium hydride is added to a solution of 5 g (0.017 mole) N-(morpholinocarbonyl)-3,4,5-trimethoxyaniline, prepared according to Example 1 or 2, in 30 ml dry dimethyl formamide. After stirring at ambient temperature until the evolution of hydrogen ceases, there are added 0.5 g sodium hydride and then, by fractions, 4.1 g (0.022 mole) 4-(2-chloroethyl)morpholine hydrochloride.

The mixture is stirred and heated to 85° C. for 10 hours.

After filtration and evaporation of solvent under vacuum, the residue is taken up in water. The aqueous phase is acidified with an N-hydrochloric acid solution, extracted with chloroform, made alkaline with sodium bicarbonate solution and extracted several times with chloroform. The organic phase is dried over sodium sulphate and concentrated under vacuum, giving 6.4 g of oily residue (93% yield).

This, dissolved in ether, is added to the necessary quantity of hydrochloric ether; the precipitate, dried, washed with dry ether and recrystallised from isopropanol, gives the pure hydrochloride:

Melting point (Tottoli)=204°-206° C.

The following Tables I, II and III contain the compounds of the preceding Examples 1 to 9 as well as other compounds prepared in an analogous manner.

TABLE I

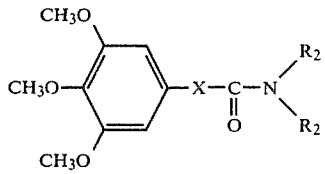

| No LJ | X | NR₁R₂ | According to Example | Yield (%) | Melting Point (°C.) | Elementary Analysis (%) Calculated | Found |
|---|---|---|---|---|---|---|---|
| 800 | NH | 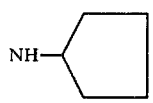 NH— | 1 | 83 | 176-77 | C 61.21<br>H 7.53<br>N 9.51 | 61.23<br>7.76<br>9.63 |

TABLE I-continued

Structure: 3,4,5-trimethoxyphenyl—X—C(=O)—NR₁R₂

| No LJ | X | NR₁R₂ | According to Example | Yield (%) | Melting Point (°C.) | Elementary Analysis (%) Calculated | Found |
|---|---|---|---|---|---|---|---|
| 801 | NH | N(CH₃)-cyclohexyl | 1 | 89 | 151–52 | C 62.31 H 7.84 N 9.08 | 62.03 7.86 9.02 |
| 778 | NH | NH-cyclohexyl | 1 | 93 | 188 | C 62.31 H 7.84 N 9.08 | 62.18 7.82 8.95 |
| 802 | NH | N(CH₃)-cycloheptyl | 1 | 84 | 197–98 | C 63.33 H 8.12 N 8.64 | 63.52 3.20 3.59 |
| 811 | NH | N(CH₂CH=CH₂)-cyclohexyl | 1 | 84 | 148 | C 65.49 H 8.10 N 8.04 | 65.40 8.13 8.14 |
| 799 | NH | NH-cycloheptyl | 1 | 84 | 202–204 | C 63.33 H 8.12 N 8.68 | 63.43 8.22 8.60 |
| 781 | NH | NH-cyclooctyl | 1 | 91 | 214–15 | C 64.26 H 8.38 N 8.32 | 64.44 8.56 8.08 |
| 813 | NH | hexamethyleneimino (—N ring) | 1 | 87 | 144–45 | C 62.32 H 7.84 N 9.08 | 62.37 7.94 8.99 |
| 820 | NH | isoxazolidino (—N—O ring) | 1 | 74 | 150–51 | C 55.31 H 6.43 N 9.92 | 55.41 6.49 9.88 |
| 733 | NH | morpholino | 1 and 2 | 92 | 154–55 | C 56.74 H 6.80 N 9.45 | 56.73 6.91 9.49 |
| 754 | O | morpholino | 3 | 65 | 118–19 | C 56.56 H 6.44 N 4.71 | 56.74 6.51 4.83 |
| 799 | NH | NH-adamantyl | 1 | 83 | 240–42 | C 66.64 H 7.83 N 7.77 | 66.50 7.94 7.58 |

TABLE I-continued $$\text{(CH}_3\text{O)}_3\text{C}_6\text{H}_2-X-\underset{\underset{O}{\|}}{C}-N(R_2)_2$$

| No LJ | X | NR₁R₂ | According to Example | Yield (%) | Melting Point (°C.) | | Elementary Analysis (%) Calculated | Found |
|---|---|---|---|---|---|---|---|---|
| 775 | NH | −N(CH₃)₂ | 1 | 68 | 144–45 | C<br>H<br>N | 56.68<br>7.13<br>11.01 | 56.88<br>7.18<br>11.05 |
| 809 | NH | −N(C₂H₅)₂ | 1 | 89 | 132 | C<br>H<br>N | 59.56<br>7.85<br>9.92 | 59.54<br>7.99<br>10.11 |
| 812 | NH | −NCH₂C(CH₃)=CH₂ | 1 | 82 | 126–27 | C<br>H<br>N | 59.99<br>7.19<br>9.99 | 59.99<br>7.35<br>9.87 |
| 780 | NH | −N((CH₂)₃CH₃)₂ | 1 | 78 | 126–27 | C<br>H<br>N | 63.87<br>8.93<br>8.27 | 64.00<br>8.94<br>8.23 |
| 810 | NH | piperidino | 1 | 90 | 173–74 | C<br>H<br>N | 59.99<br>7.19<br>9.99 | 60.14<br>7.36<br>10.17 |
| 776 | NH | hexahydroazepin-1-yl | 1 | 86 | 142–43 | C<br>H<br>N | 61.20<br>7.53<br>9.52 | 61.59<br>7.50<br>9.58 |
| 814 | NH | 4-hydroxypiperidino | 1 | 95 | 174–75 | C<br>H<br>N | 58.05<br>7.14<br>9.02 | 58.19<br>7.13<br>9.16 |
| 819 | NH | 1,2,3,6-tetrahydropyridin-1-yl | 1 | 94 | 159–60 | C<br>H<br>N | 61.63<br>6.89<br>9.58 | 61.77<br>6.93<br>9.47 |
| 879 | NH | 1,2,3,4-tetrahydroquinolin-1-yl | 1 | 92 | 164–65 | C<br>H<br>N | 66.65<br>6.48<br>8.18 | 66.65<br>6.56<br>8.15 |
| 880 | NH | 1,2,3,4-tetrahydroisoquinolin-2-yl | 1 | 90 | 135 | C<br>H<br>N | 66.65<br>6.48<br>8.18 | 66.58<br>6.64<br>8.07 |
| 816 | NH | 3-methylmorpholino | 1 | 63 | 138–39 | C<br>H<br>N | 58.05<br>7.15<br>9.03 | 58.21<br>7.25<br>9.05 |

TABLE I-continued

[Structure: 3,4,5-trimethoxyphenyl-X-C(=O)-NR₁R₂]

| No LJ | X | NR₁R₂ | According to Example | Yield (%) | Melting Point (°C.) | Elementary Analysis (%) Calculated | Found |
|---|---|---|---|---|---|---|---|
| 788 | NH | -N(CH(CH₃)CH₂)₂O (2,6-dimethylmorpholino) | 1 | 77 | 117–18 | C 59.24<br>H 7.45<br>N 8.63 | 59.19<br>7.49<br>8.51 |
| 804 | NH | thiomorpholino | 1 | 84 | 144–45 | C 53.83<br>H 6.45<br>N 8.97<br>S 10.26 | 53.84<br>6.49<br>8.93<br>10.35 |
| 759 | NH | 4-methylpiperazin-1-yl (hydrochloride) | 2 | 44 | 184–86 | C 52.09<br>H 6.99<br>N 12.15 | 51.91<br>7.12<br>11.89 |
| 767 | O | 4-methylpiperazin-1-yl (hydrochloride) | 3 | 66 | 244 | C 51.94<br>H 6.68<br>N 8.08 | 52.44<br>6.79<br>8.19 |
| 795 | NH | 4-[(4-chlorophenyl)(phenyl)methyl]piperazin-1-yl | 1 | 72 | 196–97 | C 65.38<br>H 6.09<br>N 8.47 | 65.39<br>6.12<br>8.44 |
| 840 | NH | 4-[(3,4,5-trimethoxyphenyl)carbamoyl]piperazin-1-yl | 1 | 56 | >250 | C 56.13<br>H 6.59<br>N 10.90<br>hemi-hydrate | 56.12<br>6.32<br>11.03 |
| 774 | NH | benzoxazin-4-yl (2H-1,4-benzoxazin-4-yl) | 1 | 96 | 156 | C 62.78<br>H 5.85<br>N 8.13 | 62.84<br>5.87<br>8.10 |

TABLE I-continued
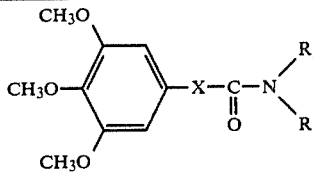
| No LJ | X | NR₁R₂ | According to Example | Yield (%) | Melting Point (°C.) | Elementary Analysis (%) Calculated | Found |
|---|---|---|---|---|---|---|---|
| 773 | O | 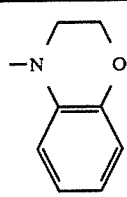 | 3 | 45 | 176 | C 62.60<br>H 5.54<br>N 4.05 | 62.78<br>5.59<br>4.06 |
| 770 | NH | 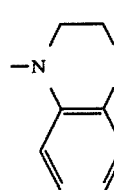 | 1 | 78 | 166–67 | C 57.07<br>H 5.05<br>N 7.39 | 57.17<br>5.21<br>7.27 |
| 798 | NH | 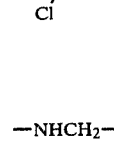 | 1 | 90 | 140–42 | C 59.10<br>H 6.44<br>N 6.89 | 59.19<br>6.53<br>6.80 |
| 783 | NH | 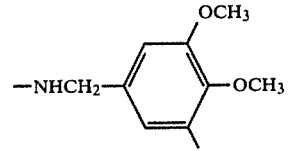 | 1 | 70 | 144–45 | C 65.43<br>H 6.71<br>N 8.47 | 65.37<br>6.64<br>8.46 |
| 796 | NH | 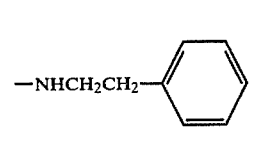 | 1 | 85 | 178–80 | C 59.26<br>H 5.80<br>N 7.67 | 59.24<br>5.81<br>7.61 |
| 797 | NH | 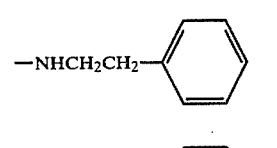 | 1 | 74 | 113–14 | C 58.05<br>H 7.14<br>N 9.02 | 58.24<br>7.23<br>8.91 |
| 815 | NH | 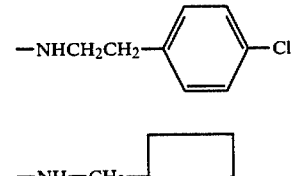 | 1 | 86 | 129–30 | C 59.24<br>H 7.46<br>N 8.63 | 59.07<br>7.24<br>8.66 |
| 877 | NH | 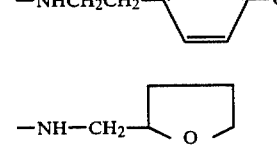 | 1 | 61 | 97–98 | C 56.13<br>H 7.65<br>N 8.18 | 55.98<br>7.77<br>8.04 |
| 784 | NH | 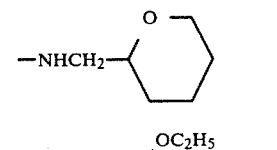 | 1 | 78 | 117–18 | C 57.86<br>H 8.09<br>N 13.49 | 57.98<br>8.22<br>13.53 |
|  | NH | 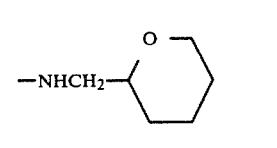 | 1 | 94 | 144–45<br>(HCl) 195 | C 56.62<br>H 7.42<br>N 12.38 | 56.58<br>7.65<br>12.20 |

TABLE I-continued

Structure: 3,4,5-trimethoxyphenyl-X-C(=O)-NR₁R₂

| No LJ | X | NR₁R₂ | According to Example | Yield (%) | Melting Point (°C.) | Elementary Analysis (%) Calculated | Found |
|---|---|---|---|---|---|---|---|
| 785 | NH | NH(CH₂)₃N(CH₃)₂ | 1 | 80 | 86–87 | C 57.86<br>H 8.09<br>N 13.49 | 57.83<br>8.23<br>13.29 |
| 805 | NH | (CH₃)N—(CH₂)₃—N(CH₃)₂ | 1 | 63 | 81–83 | C 59.05<br>H 8.36<br>N 12.95 | 59.19<br>8.38<br>12.97 |
| 777 | NH | —NH-(7-chloroquinolin-4-yl) | 1 | 68 | 228–230 | C 58.84<br>H 4.68<br>N 10.83 | 58.70<br>4.66<br>10.73 |
| 830 (HCl) | NH | piperazinyl-CH₂-C(=O)-piperidinyl | 1 | 62 | 150 | C 59.98<br>H 7.67<br>N 13.32 | 60.16<br>7.70<br>13.27 |
| 821 | —N(CH₂Ph)— | morpholino | 9 | 78 | 101–103 | C 65.27<br>H 6.78<br>N 7.25 | 65.16<br>6.63<br>7.27 |
| 822 (hydrochloride) | —N(CH₂CH₂-morpholino)— | morpholino | 9 | 93 | 204–206 | C 53.87<br>H 7.23<br>N 9.42 | 53.56<br>7.16<br>9.54 |

TABLE II

Structure: 3,4,5-trimethoxyphenyl-NH-(CH₂)ₘ-Y-NR₁R₂

| No LJ | Y | NR₁R₂ | m | According to Example | Yield (%) | Melting Point (°C.) | Elementary Analysis (%) Calculated | Found |
|---|---|---|---|---|---|---|---|---|
| 793 | CO | morpholino | 1 | 7 | 89 | 136 | C 58.05<br>H 7.14<br>N 9.03 | 58.00<br>7.17<br>8.98 |

TABLE II-continued $$CH_3O-\underset{\underset{CH_3O}{|}}{\overset{\overset{CH_3O}{|}}{C_6H_2}}-NH-(CH_2)_m-Y-N\overset{R_1}{\underset{R_2}{\diagup}}$$

| No LJ | Y | NR₁R₂ | m | According to Example | Yield (%) | Melting Point (°C.) | Elementary Analysis (%) | Calculated | Found |
|---|---|---|---|---|---|---|---|---|---|
| 837 | CO | −N(piperazine)N−phenyl | 1 | 7 | 51 | 147 | C<br>H<br>N | 65.43<br>7.06<br>10.90 | 65.42<br>7.18<br>11.21 |
| 786 | CO | −N(piperazine)N−CH₃ | 1 | 7 | 47 | 156–158 | C<br>H<br>N | 59.43<br>7.79<br>13.00 | 59.31<br>7.82<br>13.05 |
| 782 (HCl:839) | CO | −N(benzomorpholine)O | 1 | 7 | 41 | 129 | C<br>H<br>N | 63.67<br>6.13<br>7.81 | 63.75<br>6.13<br>7.73 |
| 762 | CO | −N(chlorobenzomorpholine)O, Cl | 1 | 7 | 52 | 178 | C<br>H<br>N | 58.09<br>5.39<br>7.13 | 58.18<br>5.40<br>7.03 |

TABLE III $$CH_3O-\underset{\underset{CH_3O}{|}}{\overset{\overset{CH_3O}{|}}{C_6H_2}}-NH-Y-(CH_2)_m-NR_1R_2$$

| No LJ | Y | NR₁R₂ | n | According to Example | Yield (%) | Melting Point (°C.) | Elementary Analysis (%) | Calculated | Found |
|---|---|---|---|---|---|---|---|---|---|
| 807 | −C(=O)−NH− | −N(morpholine)O | 0 | 4 | 94 | 204 | C<br>H<br>N | 54.01<br>6.80<br>13.49 | 53.97<br>6.82<br>13.55 |
| 828 | −C(=O)−O− | −N(morpholine)O | 0 | 4 | 82 | 160–61 | C<br>H<br>N | 53.84<br>6.45<br>8.97 | 53.65<br>6.36<br>9.03 |
| 787 phosphate 833 | CO | −N(morpholine)O | 1 | 8 | 56 | 110–11 | C<br>H<br>N | 58.05<br>7.14<br>9.03 | 57.96<br>7.22<br>8.90 |
| 817 | CO | −N(morpholine)O | 2 | 8 | 81 | 113–14 | C<br>H<br>N | 59.24<br>7.46<br>8.63 | 59.16<br>7.51<br>8.70 |

TABLE III-continued $$CH_3O-\underset{\underset{CH_3O}{|}}{\overset{\overset{CH_3O}{|}}{\bigcirc}}-NH-Y-(CH_2)_m-NR_1R_2$$

| No LJ | Y | NR₁R₂ | n | According to Example | Yield (%) | Melting Point (°C.) | Elementary Analysis (%) Calculated | Found |
|---|---|---|---|---|---|---|---|---|
| 792 | CO | −N⌐O (morpholino-phenyl) | 1 | 8 | 43 | 159 | C 63.67<br>H 6.13<br>N 7.81 | 63.58<br>6.16<br>7.79 |
| 818 | −C(=O)−O | −N⌐O (morpholine) | 2 | 5 | 67 | 81–82 | C 56.46<br>H 7.11<br>N 8.23 | 56.43<br>7.08<br>8.16 |
| 791 | SO₂ | −N⌐O (morpholine) | 0 | 6 | 47 | 148 | C 46.98<br>H 6.06<br>N 8.43 | 47.03<br>6.16<br>8.42 |
| 881 | CO | −N (piperidine) | 1 | 8 | 42 | 81–82 | C 62.32<br>H 7.84<br>N 9.08 | 62.45<br>7.88<br>9.08 |
| 829 | CO | −N−piperidine−OH, 4-chlorophenyl | 2 | 8 | 68 | 227 (hydrochloride) | C 52.97<br>H 6.57<br>N 6.57 | 53.10<br>6.28<br>5.39 (hydrochloride dihydrate) |
| 838 (HCl) | CO | −N piperazine-N-(3-CF₃-phenyl) | 1 | 8 | 70 | 240 (hydrochloride) | C 58.27<br>H 5.78<br>N 9.27 | 58.07<br>5.85<br>9.12 |
| 841 | CO | N piperazine N-(3-CF₃-phenyl) | 2 | 8 | 72 | 238–40 (hydrochloride) | C 54.81<br>H 5.80<br>N 8.34 | 54.66<br>5.91<br>8.23 (hydrochloride) |
| 848 | CO | N piperazine N−CH₂C(=O)NH−(3,4,5-trimethoxyphenyl) | 1 | 8 | 85 | 228–30 (dihydrochloride) | C 51.57<br>H 6.32<br>N 9.25 | 51.26<br>6.47<br>9.23 (dihydrochloride) |
| 834 | CONHCO | −N⌐O (morpholine) | 1 | 7 | 92 | 136–38<br>HCl<br>212–214 | C 54.39<br>H 6.56<br>N 11.89 | 54.35<br>6.56<br>11.47 |

The compounds of the invention have been subjected to pharmacological tests. Acute toxicity of different compounds has been determined and their activity in the region of the central nervous system has been tested.

1—ACUTE TOXICITY FOR ORAL ADMINISTRATION IN MICE

The compounds are administered orally in increasing doses in suspension in a 10% gum arabic solution to groups of 5 ♀ mice of mean weight 25 g. The 50% lethal doses (LD 50) are calculated by the method of KARBER and BEHRENS (Arch. Exp. Path. Pharmakol. 1935, 177, 379-388).

The LD 50's found are summarised in Table IV below and indicate that the tested compounds have low toxicity.

2—ACTIVITY IN THE REGION OF THE CENTRAL NERVOUS SYSTEM

2.1—Action on spontaneous motor activity in the mouse

This test has been carried out according to the method of BOISSIER (Arch. Int. Pharmacodyn. 1945, 158, 212). 30 minutes after administration per os of the test compounds, the mice (groups of 12 animals) are installed in individual cages in a BOISSIER activity measuring cupboard and move about before two photoelectric cells placed according to the rectangular coordinates. Meters register the movement during 20 minutes. The mean number of movements are calculated for the control group and the treated groups and the variations in motor activity of the treated groups are expressed as percentages based on the results for the control group.

Table V below shows that the test compounds reduce spontaneous motor activity in the mouse.

2.2—Action on the pentobarbital hypnosis time in the mouse 30 minutes after administration per os of the compounds, the mice (groups of 10 animals) receive an injection of pentobarbital at a dose (50 mg/kg i.v.) which dose causes the control animals, which have received only administration vehicle (i.e. 10% gum arabic solution), to sleep for about 30 to 60 minutes. The hypnosis time of each mouse is counted in minutes from the moment when the animal may be placed without resistance on its back until that when it spontaneously gets back on its feet. In the treated groups and the control group, the average hypnosis times are calculated and the results obtained in the treated groups are expressed as percentages of the variation of hypnosis time based on the control group.

The results of Table VI below show that the test compounds increase the narcotic effect of pentobarbital.

2.3—Test on the action against the convulsant effects of electric shock and of strychnine in the mouse 30 minutes after administration of the compounds to groups of 10 animals, there is investigated the protection induced against:

tonic crisis (extension of rear feet) provoked by supramaximal transcranial electric stimulation (13 to 16 mA for 0.1 sec).

convulsive crisis and death provoked by injection of strychnine at a limiting lethal dose of 1.5 mg/kg s.c.

The results are expressed as a percentage of protection based on a control group which have only received the administration vehicle for the compounds.

The results of Tables VII and VIII show that the test compounds at to reduce, in a manner more or less intense, the convulsant effects of strychnine and of electric shock.

TABLE IV
ACUTE TOXICITY FOR ALL ADMINISTRATION IN MICE

| Compounds | LD 50 in mg/kg |
| --- | --- |
| 767 | 1025 |
| 793 - 820 | 1250 |
| 788 | 1350 |
| 775 - 786 | 1700 |
| 812 | 2000 |
| 785 | 2200 |
| 787 - 801 - 805 - 807 -816 - 821 | 2500 |
| 809 - 813 - 833 | 3000 |
| 784 - 834 | 3375 |
| 818 | 3500 |
| 776 - 810 | 3750 |
| 733 - 759 | 4000 |
| 797 | 4400 |
| 754 - 811 - 814 - 815 - 817 - 819 - 822 - 830 | 5000 |
| 762 - 770 - 773 - 774 - 777 - 778 - 779 - 780 - 781 - 782 - 783 - 791 - 792 - 795 - 796 - 798 - 799 - 800 - 802 - 804 - 828 - 829 - 837 - 838 - 839 - 840 - 841 - 848 | >5000 |

TABLE V
ACTION ON SPONTANEOUS MOTOR ACTIVITY IN THE MOUSE

| Compounds Nos. LJ | Doses in mg/kg p.o. | Pecentage variation in motor activity (%) |
| --- | --- | --- |
| 733 | 400 | −74 |
| 754 | 500 | −41 |
| 759 | 400 | −45 |
| 775 | 170 | −40 |
| 776 | 375 | −48 |
| 786 | 170 | −20 |
| 787 | 250 | −84 |
| 788 | 135 | −34 |
| 789 | 250 | −62 |
| 790 | 125 | −37 |
| 791 | 500 | −53 |
| 798 | 500 | −20 |
| 801 | 250 | −29 |
| 804 | 500 | −24 |
| 807 | 250 | −33 |
| 809 | 300 | −78 |
| 810 | 375 | −38 |
| 817 | 500 | −17 |
| 818 | 350 | −33 |
| 819 | 500 | −18 |

TABLE VI
ACTION ON THE PENTOBARBITAL HYPNOSIS TIME IN THE MOUSE

| Compounds Nos. LJ | Doses in mg/kg p.o. | Percentage variation in pentobarbitol hypnosis time (%) |
| --- | --- | --- |
| 733 | 400 | +164 |
| 754 | 500 | +178 |
| 759 | 400 | +22 |
| 775 | 170 | +149 |
| 776 | 375 | +130 |
| 786 | 170 | +172 |
| 787 | 250 | +141 |
| 790 | 125 | +270 |
| 791 | 500 | +200 |
| 798 | 500 | +145 |
| 801 | 250 | +70 |
| 804 | 500 | +120 |
| 807 | 250 | +98 |
| 809 | 300 | +157 |
| 810 | 375 | +148 |
| 817 | 500 | +300 |
| 818 | 350 | +180 |

TABLE VII

ACTION AGAINST THE CONVULSANT EFFECTS OF STRYCHNINE IN THE MOUSE

| Compound Nos. LJ | Doses in mg/kg p.o. | Percentage protection against the convulsant effects of strychnine (%) |
|---|---|---|
| 733 | 400 | 100 |
| 754 | 500 | 100 |
| 759 | 400 | 55 |
| 775 | 170 | 33 |
| 776 | 375 | 44 |
| 789 | 250 | 78 |
| 790 | 125 | 78 |
| 801 | 250 | 100 |
| 819 | 500 | 70 |

TABLE VIII

ACTION AGAINST THE CONVULSANT EFFECTS OF ELECTRIC SHOCK IN THE MOUSE

| Compounds Nos. LJ | Doses in mg/kg p.o. | Percentage protection against the convulsant effects of the electric shock (%) |
|---|---|---|
| 733 | 400 | 30 |
| 754 | 500 | 90 |
| 798 | 500 | 40 |
| 801 | 250 | 37 |
| 809 | 300 | 80 |
| 810 | 375 | 70 |
| 817 | 500 | 40 |
| 819 | 500 | 40 |

These results shows that the compounds of the invention possess tranquillising, sedative and myorelaxant effects. They are thus appropriate in the treatment of psychosomatic affections.

The theraputic indications of the compounds of the invention concern:
anxiety, hyperemotivity, neurotic states, character troubles,
functional troubles, neurovegative dystonis,
contractions of muscular origin, lumbagos, torticollis, painful cramps etc.

The compounds of the invention may be administered orally, rectally, parenterally, by aerosol or may be used externally.

For oral administration the mean posology is 1 to 3 g per day for an adult.

Preferred pharmaceutical forms are tablets, capsules, syrups, drinkable suspensions, suppositories, injectable solutions, aerosols, skin creams, liniments etc.

We claim:

1. A compound of the formula

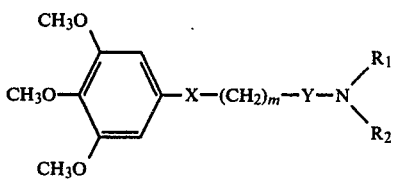

wherein
m is selected from O and the numbers 1 and 2,
X is selected from oxygen and an imino group of the formula $NR_3$, (wherein $R_3$ is selected from hydrogen benzyl, and morpholinoethyl),
Y is selected from the divalent groups CO, CONH, and COO and $SO_2$, and
$NR_1R_2$ is selected from the group consisting of morpholino, 2-methylmorpholino, 2,6-dimethylmorpholino, 2-morpholinoethylamino, and thiamorpholino,
and their pharmaceutically-acceptable acid addition salts.

2. A compound according to claim 1 which is of the formula

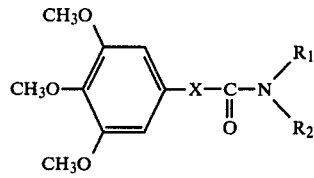

(wherein X and $NR_1R_2$ are as defined in claim 1) and its pharmaceutically-acceptable acid addition salts.

3. A compound according to claim 1 which is of the formula

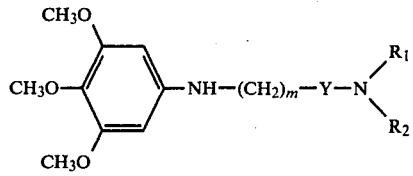

(wherein Y, m and $NR_1R_2$ are as defined in claim 1) and its pharmaceutically-acceptable acid addition salts.

4. A compound according to claim 1 wherein $NR_1R_2$ represents a morpholino or 2,6-dimethylmorpholino.

5. A compound according to claim 1 which is selected from 4-[N-(3,4,5-trimethoxyphenyl)-carbamoyl]-morpholine and 4-(3,4,5-trimethoxyphenoxycarbonyl)-morpholine.

6. 4-(3,4,5-Trimethoxyphenoxycarbonyl)-morpholine, and its pharmaceutically-acceptable acid addition salts.

7. 4-[N-(3,4,5-trimethoxyphenyl)-carbamoyl]-morpholine, and its pharmaceutically-acceptable acid addition salts.

8. A pharmaceutical composition, useful for its tranquilizing, muscle relaxing and sedative effects, which comprises a pharmaceutically effective amount of a compound of claim 1, or a pharmaceutically acceptable acid-addition salt thereof together with a pharmaceutically acceptable carrier or diluent.

9. A pharmaceutical composition according to claim 7 which contains a compound selected from 4-[N-(3,4,5-trimethoxyphenyl)-carbamoyl]-morpholine and 4-(3,4,5-trimethoxyphenoxycarbonyl)-morpholine.

10. A method for treating a human patient which comprises administering to said patient for its tranquilizing, muscle relaxing and sedative effects, a therapeutically-effective amount of a compound of claim 1 or a pharmaceutically-acceptable acid-addition-salt thereof.

11. A method according to claim 10 wherein there is administered a compound selected from 4-[N-(3,4,5-trimethoxyphenyl)-carbamoyl]-morpholine and 4-(3,4,5-trimethoxyphenoxycarbonyl)-morpholine.

* * * * *

UNITED STATES PATENT AND TRADEMARK OFFICE
CERTIFICATE OF CORRECTION

PATENT NO. : 4,252,804

DATED : February 24, 1981

INVENTOR(S) : Maurice Jouillié, Gabriel Maillard, Lucien Lakah and Christian J. M. Warolin It is certified that error appears in the above-identified patent and that said Letters Patent are hereby corrected as shown below:

Col. 2, first formula, between lines 5 & 13 and the second formula, between lines 17 & 25, should switch places.

Col. 2, line 14; "X" should read -- Y --

Cols. 9 and 10, Table 1-continued, last column, third group of numbers down, second and third numbers; "3.20 / 3.59" should read -- 8.20 / 8.59 --

Cols. 21 and 22, next to last column titled "Calculated", fifth group of numbers down, third line in group; "6.57" should read -- 5.37 --

Col. 26, line 2; "NR$_3$, (wherein" should read -- -NR$_3$, wherein --

Col. 26, line 3; delete the ")" in "morpholinoethyl),"

Col. 26, line 5; delete "and" (first occurrence)

Signed and Sealed this

Fourteenth Day of July 1981

[SEAL]

Attest:

GERALD J. MOSSINGHOFF

Attesting Officer

Commissioner of Patents and Trademarks